United States Patent [19]

Rosen

[11] 4,143,227
[45] Mar. 6, 1979

[54] PROCESS FOR SUBSTITUTED 5-BENZYL-2,4-DIAMINO-PYRIMIDINES

[75] Inventor: Perry Rosen, North Caldwell, N.J.

[73] Assignee: Hoffmann-La Roche Inc., Nutley, N.J.

[21] Appl. No.: 805,506

[22] Filed: Jun. 10, 1977

Related U.S. Application Data

[63] Continuation of Ser. No. 564,518, Apr. 2, 1975, abandoned, which is a continuation of Ser. No. 336,094, Feb. 26, 1973, abandoned.

[51] Int. Cl.² ............... C07D 239/48; A61K 31/505
[52] U.S. Cl. .................................. 544/325; 424/251
[58] Field of Search ................. 260/256.4 N; 544/325

[56] References Cited

U.S. PATENT DOCUMENTS 3,485,840  12/1969  Hoffer .................... 260/256.4 N

OTHER PUBLICATIONS

Wagner, et al., Synthetic Organic Chemistry, 1953, John Wiley & Sons, Inc. pp. 2-3.

Primary Examiner—Jose Tovar
Assistant Examiner—James H. Turnipseed
Attorney, Agent, or Firm—Jon S. Saxe; George M. Gould; William G. Isgro

[57] ABSTRACT

A process for preparing a compound of the formula

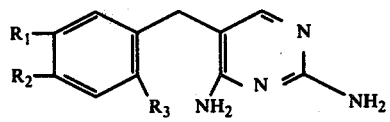

wherein $R_1$ and $R_2$ are lower alkoxy or taken together are methylenedioxy; $R_3$ is lower alkyl or hydrogen, which comprises the step of reacting an aromatic compound of the formula

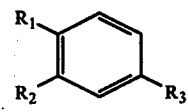

wherein $R_1$, $R_2$ and $R_3$ are as previously described, with a diamino-pyrimidine of the formula

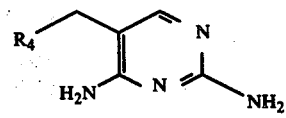

wherein $R_4$ is lower alkoxy, benzyloxy, hydroxy or halogen, in the presence of an inorganic or organic acid selected from the group consisting of ortho-phosphoric acid, poly-phosphoric acid, hydrohalic acids and tri-haloacetic acids, at a temperature in the range of from about 50° C. to about 110° C., is described.

2 Claims, No Drawings

PROCESS FOR SUBSTITUTED 5-BENZYL-2,4-DIAMINO-PYRIMIDINES

CROSS REFERENCE TO RELATED APPLICATIONS

This is a continuation of application Ser. No. 564,518 filed Apr. 2, 1975, now abandoned, which in turn is a continuation of U.S. Patent Application Ser. No. 336,094 filed Feb. 26, 1973, now abandoned.

BRIEF SUMMARY OF THE INVENTION

The invention relates to a process for preparing compounds of the formula

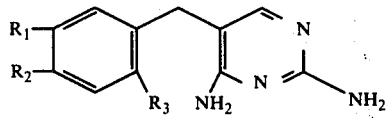

I wherein $R_1$ and $R_2$ are lower alkoxy or taken together are methylenedioxy; $R_3$ is lower alkyl or hydrogen, or pharmaceutically acceptable acid addition salts thereof, which comprises condensing α-alkoxy-methylene-β-methoxypropionitrile with guanidine an subsequently reacting the so-formed pyrimidine of the formula

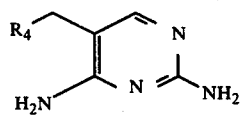

III wherein $R_4$ is lower alkoxy, benzyloxy, hydroxy or halogen,
with the appropriately substituted aromatic compound of the formula

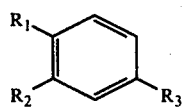

II wherein $R_1$, $R_2$ and $R_3$ are as previously described.

In another aspect, the invention relates to compounds of the formula

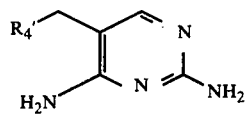

IIIa wherein $R_4'$ is lower alkoxy, benzyloxy or halogen.

Detailed Description of the Invention

As used herein, the term "lower alkyl" denotes a straight or secondary branched chain saturated hydrocarbon containing from 1-7 carbon atoms, for example, methyl, ethyl, propyl, isopropyl, butyl pentyl, heptyl or the like. The term "lower alkoxy" denotes an alkyl ether group in which the lower alkyl group is as described above, for example, methoxy, ethoxy, propoxy, pentoxy and the like. The term "halogen" denotes all the halogens, i.e., bromine, chlorine, fluorine and iodine.

The invention relates to a process for preparing the compounds of the formula

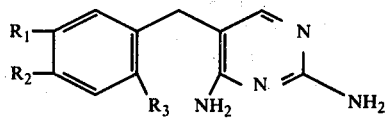

I wherein $R_1$ and $R_2$ are lower alkoxy or taken together are methylendioxy; and $R_3$ is lower alkyl or hydrogen,
which comprises reacting a benzene derivative of the formula

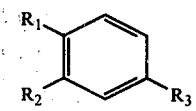

II wherein $R_1$, $R_2$ and $R_3$ are as previously described, with a 2,4-diamino-pyrimidine derivative of the formula

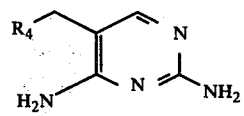

III wherein $R_4$ is as previously described, in the presence of an inorganic acid, for example, orthophosphoric acid, poly-phosphoric acid, hydrohalic acid, such as hydrochloric acid, hydrobromic acid or the like, or an organic acid, for example, trihaloacetic acid, such as trifluoroacetic acid, or the like.

The reaction is carried out at a temperature in the range of from about 50° to about 110° C. If desired, an inert organic solvent can be utilized but is not necessarily required. Generally, the inorganic or organic acid utilized in the reaction also acts as the solvent. The resulting acid addition salt of a compound of the formula

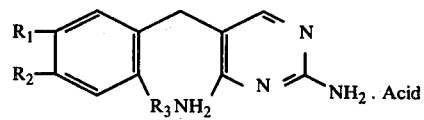

I wherein $R_1$, $R_2$ and $R_3$ are as previously described, and Acid is an inorganic or organic acid as described above,
is thereafter recovered by conventional methods and subsequently purified by conventional methods such as, for example, crystallization, filtration, and the like. If the base compound is desired, it can be obtained by neutralization of the acid salt, for example, with alkali metal hydroxide or the like.

Exemplary of the compounds of formula II are:
3,4-dimethoxytoluene;
1,2-dimethoxybenzene;
3,4-diethoxytoluene;
1,2-methylenedioxybenzene;
3,4-methylenedioxytoluene; and the like.

Exemplary of the compounds of formula III are:
2,4-diamino-5-methoxymethyl-pyrimidine;
2,4-diamino-b 5-ethoxymethyl-pyrimidine;
2,4-diamino-5-hydroxymethyl-pyrimidine;
2,4-diamino-5-chloromethyl-pyrimidine;
2,4-diamino-5-bromomethyl-pyrimidine;
2,4-diamino-5-fluoromethyl-pyrimidine, and the like.

The 2,4-diamino-pyrimidine of formula III wherein $R_4$ is lower alkoxy or benzyloxy, i.e., the compounds of the formula

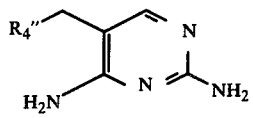   IIIb wherein $R_4''$ is lower alkoxy (preferably methoxy) or benzyloxy,
can be prepared by reacting a β-alkoxy-propionitrile of the formula

   IV wherein $R_4''$ is as previously described, with methylformate

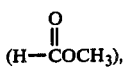, utilizing an alkali metal alcoholate, for example, alkali metal alkoxide, such as sodium methoxide, potassium methoxide, or the like, or alkali metal benzyloxide. The reaction is conveniently carried out in an inert organic solvent, for example, a hydrocarbon, such as toluene, benzene, xylene or the like, at a temperature in the range of from about 25° to about 100° C., preferably from about 40° to about 70° C. and at a pressure in the range of from about 20 to 50 atmospheres of carbon monoxide.

The resulting α-alkoxymethylene-propionitrile of the formula

   VI wherein $R_4''$ is as previously described,
is recovered from the reaction mixture utilizing conventional methods, for example, by crystallization, distillation; most preferably, by distillation.

It should be noted that the compounds of formula VI exist in two isomeric forms (cis-trans), i.e.,

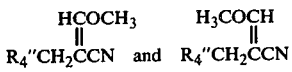

wherein $R_4''$ is as previously described.

For the purposes of the invention, the isomers need not be separated but can be utilized as a mixture in the next reaction step. Thereafter, the α-alkoxymethylene-β-methoxypropionitrile of the formula

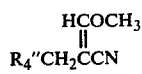   VI wherein $R_4''$ is as previously described,
is reacted with guanidine or guanidine carbonate to yield the 2,4-diamino-pyrimidine of the formula

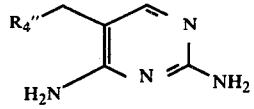   IIIb wherein $R_4''$ is as previously described.
Exemplary of the compounds of formula IV are:
β-methoxy-propionitrile;
β-ethoxy-propionitrile;
β-propoxy-propionitrile; and the like.

Exemplary of the compounds of formula VI are:
α-methoxymethylene-β-methoxy-propionitrile;
α-ethoxymethylene-β-methoxy-propionitrile;
α-propoxymethylene-β-methoxy-propionitrile; and the like.

A 2,4-diamino-pyrimidine of formula III wherein $R_4$ is halogen, i.e., a compound of the formula

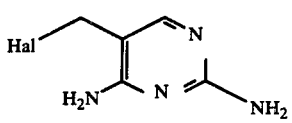   IIIc wherein Hal is halogen, can be prepared by reacting as a compound of the formula

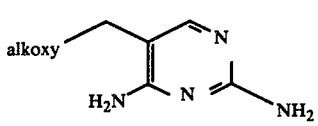   IIId with a hydrohalic acid, i.e., HX, in a solvent, for example, an alkanol such as butanol, pentanol or the like, or dimethylsulfoxide or the like.

The 2,4-diamino-pyrimidine of formula III wherein $R_4$ is hydroxy, i.e., 2,4-diamino5-hydroxymethyl-pyrimidine can be prepared by treating the corresponding 2,4-diamino-5-halomethylpyrimidine with an aqueous carbonate, such as silver carbonate or the like, at a temperature in the range of from about 0° to about 25° C., and thereafter recovering the desired end-product by known procedures, such as extraction or the like.

The pyrimidines of formula I are known compounds and are useful as potentiators of sulfonamides.

The compounds of formula I are useful in combination with one or more sulfa drugs, such as, for example, $N^1$-(3,4-dimethyl-5-isoxazolyl)-sulfanilamide, 5-methyl-3-sulfanilamido-isoxazole, $N^1$-(2,6-dimethoxy-4-pyrimidinyl)-sulfanilamide, $N^4$-ethoxyacetyl-$N^1$-(5methyl-3-isoxazolyl)-sulfanilamide, $N^1$-(4,5-dimethyl-3-isoxazolyl)sulfanilamide, $N^1$-(5,6-dimethoxy-4-pyrimidinyl)-sulfanilamide and the like as antibacterial agents. The addition of a compound of formula I to one of the above-mentioned sulfonamides results in a marked potentiation of the antibacterial activity of the sulfonamide. Thus, the compounds of formula I are useful as potentiators of sulfonamides.

The compounds prepared by the process of the invention can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkyleneglycols and the like. The pharmaceutical preparations can be employed in a solid form, for example, as tablets, troches, suppositories, capsules or in liquid form, for example, as solutions, suspensions or emulsions. The pharmaceutical adjuvant material can be added and can include preservatives, stabilizers, wetting or emulsifying agents, salts to change the osmotic pressure or to act as buffers. They can also contain other therapeutically active materials.

The following examples further illustrate the invention. All temperatures are in degrees Centigrade, unless otherwise mentioned.

EXAMPLE 1

Preparation of α-methoxymethylene-β-methoxypropionitrile

To an autoclave sleeve charged with 63.4 g. of sodium methoxide and 347 ml. of anhydrous toluene was added in four portions at 5–10°, 94.5 g. of β-methoxypropionitrile. At the same temperature, 67 g. of methyl formate was then added in two portions. The mixture was heated to 50° under 50 atmospheres of carbon monoxide for 19 hours. The reaction was cooled to room temperature, flushed with nitrogen and the pale brown solid filtered through a coarse sintered glass funnel under nitrogen. The precipitate was washed with 90 ml. of anhydrous toluene, transferred to a 1-liter round bottom flask and dried to constant weight on an evaporator at 50° using at first a water aspirator and then a high vacuum pump. To a slurry of the dried sodium salt (145.6 g.) in 400 ml. of anhydrous toluene was added 110 ml. of dimethylsulfate. The resulting mixture was then heated at 50° for 15 hours, cooled to room temperature and 20.8 ml. of triethylamine added. After stirring for half hour 190 ml. of a 20 percent w/v sodium chloride solution diluted with 30 ml. of water was added and the resulting suspension stirred for 10 minutes. The emulsion was allowed to separate and the water layer drawn off and saved. The toluene layer was then washed with 65 ml. of a 20 percent w/v sodium chloride solution and the aqueous solution separated and combined with the previous aqueous wash. The combined water solutions were then extracted with 2 × 130 ml. of toluene. The toluene fractions were combined, dried over calcium chloride and the solvent evaporated to give 152.8 g. of crude α-methoxymethylene-β-methoxypropionitrile, as a pale yellow oil. The oil was then distilled through a 4 inch Vigreaux column under reduced pressure.

| Fraction | mm | Vapor Temp. | Pot. Temp. | Weight | Color |
|---|---|---|---|---|---|
| 1 | 0.2–1.5 | 78–84° | 125–132° | 23.5 g. | colorless |
| 2 | 0.15 | 84–89° | 132–137° | 29.0 g. | colorless |
| 3 | 0.15 | 89–91° | 137° | 59.5 g. | faint yellow |

The first fraction consists of one isomer; second fraction is a mixture of isomers, and third fraction is a second isomer. All fractions are combined and used for the next reaction.

EXAMPLE 2

Preparation of 2,4-diamino-5-methoxymethyl pyrimidine

A solution of 318 g. of α-methoxymethylene-β-methoxypropionitrile, 270 g. of guanidine carbonate and 1 l. of dimethylformamide was refluxed for 4.5 hours. At the end of this time, the dimethylformamide was removed under high vacuum and the resulting residue treated with 1650 ml. of an aqueous solution containing 102.3 g. of sodium hydroxide. The mixture was then refluxed for 1 hour. At the end of the reflux period, the dark brown solution was cooled to room temperature and 190 g. of sodium chloride was added. The mixture was stirred and cooled to 5–10° at which time there appeared a copious precipitate of 2,4-diamino-5-methoxymethyl pyrimidine. The product was filtered and washed with ice water to give 302 g. of light yellow crude 2,4-diamino-5-methoxymethyl pyrimidine, having a melting point of 171°–174° (uncorrected). The water washings and the filtrate were then combined and extracted for 48 hours with methylene chloride in a liquid-liquid extractor. Evaporation of the methylene chloride afforded an additional 57 g. of yellow crystalline material having a melting point of 140°–144°. Purification of the material was not attempted. A homogeneous mixture of 30 g. of crude 2,4-diamino-5-methoxymethylpyrimidine (mp 171°–174°) and 6 g. of charcoal was placed in a Soxhlet cup and extracted with 1 l. of acetone for 36 hours. The hot solution was then filtered and the acetone evaporated to give a slightly yellow product. Trituration with a small amount of cold acetone afforded 24.6 g. of white crystalline 2,4-diamino-5-methoxymethyl pyrimidine, having a melting point of 174°–176°. Crystallization from methanol afforded an analytical sample of melting point 176°–178°.

Analysis Calcd. for $C_6H_{10}N_4O$: C, 46.74; H, 6.54; N, 36.34 Found: C, 46.69; H, 6.65; N, 36.37

EXAMPLE 3

Preparation of 2,4-diamino-5-(4,5-dimethoxy-2-methylbenzyl)pyrimidine

A mixture of 12.3 g. of 2,4-diamino-5-methoxymethylpyrimidine, 11 g. of 3,4-dimethoxytoluene and 72 g. of orthophosphoric acid was heated with good stirring at 110° for 4.5 hours. At the end of this time, the reaction was cooled, 30 ml. of water added, and the resulting solution added dropwise with stirring to 195 ml. of a cooled (0°) 50 percent potassium hydroxide solution. The resulting mixture was then allowed to digest in the refrigerator overnight and then was filtered. The residue was washed with small portions of ice water until the filtrate reached a pH 8–9. The resulting off-white colored solid was dried in a vacuum oven at 50° for 3 hours to give 20.5 g. of crude 2,4-diamino-5-(4,5-dimethoxy-2-methylbenzyl)-pyrimidine (104 percent of theory), melting point 217°–222°. This material was then crystallized from 60 ml. of dimethylformamide and 2 g. of charcoal. The filtrate was cooled to room temperature and placed in the refrigerator overnight. Thereafter, the residue was filtered and washed with a small amount of cold dimethylformamide to give 14.6 g. (74 percent) of 2,4-diamino-5-(4,5-dimethoxy-2-methylbenzyl)-pyrimidine, having a melting point of 230°–232°.

EXAMPLE 4

Preparation of 2,4-diamino-5-(3,4-dimethoxybenzyl)pyrimidine

A mixture of 12.3 g. of 2,4-diamino-5-methoxymethylpyrimidine, 10.9 g. of veratrole and 72 g. of orthophosphoric acid was stirred and heated at 110° for 4 hours. The resulting thick yellow solution was dissolved in 40 ml. of water and the formed solution slowly added to 190 ml. of a 50 percent potassium hydroxide solution at 10°–15°. A white precipitate formed and the mixture was allowed to digest in the refrigerator overnight. The precipitate was removed by filtration and the solid washed with ice water until the washings reached a pH 8. The product was then dissolved in a solution comprised of 50 ml. of glacial acetic acid and 175 ml. of water. The resulting yellow turbid solution was treated with charcoal and filtered. The resudue was washed with 100 ml. of water. The aqueous solutions were combined and treated dropwise at 0° with 190 ml. of a solution prepared from 40 g. of sodium hydroxide and 200 ml. of water. The precipitate was removed by filtration, washed with water and air-dried to give 17.2 g. of 2,4-diamino-5-(3,4-dimethoxybenzyl)pyrimidine (88.7 percent) having a melting point of 227°–230°.

EXAMPLE 5

Preparation of 2,4-diamino-5-(2-n-propyl-4,5-dimethoxybenzyl)-pyrimidine

A mixture of 1.2 g. of 1,2-dimethoxy-4-n-propylbenzene, 1 g. of 2,4-diamino-5-methoxymethyl pyrimidine and 10 g. of orthophosphoric acid was stirred and heated at 110° for 4.5 hours. The mixture was then dissolved in 10 ml. of water and added dropwise at 10°–15° to 18 ml. of a 50 percent potassium hydroxide solution (12.8 mmol of potassium hydroxide). The precipitate was removed by filtration, dissolved in methylene chloride and dried with magnesium sulfate. The solvent was removed and the solid residue (1.9 g.) crystallized from ethyl acetate to give 1.7 g. of 2,4-diamino-5-(2-n-propyl-4,5-dimethoxybenzyl)-pyrimidine, m.p. 166°–167°.

Analysis Calcd. for $C_{16}H_{22}N_4O_2$: C, 63.55; H, 7.30; N, 18.53 Found: C, 63.59; H, 7.50; N, 18.61

I claim:

1. A process for preparing a compound of the formula

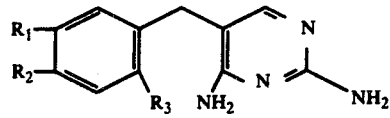

wherein $R_1$ and $R_2$ are lower alkoxy or taken together are methylenedioxy; $R_3$ is lower alkyl or hydrogen, which comprises the step of reacting an aromatic compound of the formula

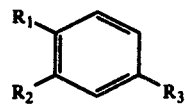

wherein $R_1$, $R_2$ and $R_3$ are as previously described, with a diamino-pyrimidine of the formula

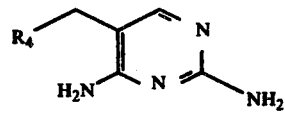

wherein $R_4$ is lower alkoxy, benzyloxy, hydroxy or halogen, in the presence of an inorganic or organic acid selected from the group consisting of ortho-phosphoric acid, poly-phosphoric acid, hydrohalic acids and trihaloacetic acids, at a temperature in the range of from about 50° C. to about 110° C.

2. A process in accordance with claim 1, wherein the acid is orthophosphoric acid.

* * * * *